United States Patent [19]

Menapace et al.

[11] 4,017,552

[45] Apr. 12, 1977

[54] BICYCLO-[3'3'0]-OCTA-2-ENE FORMED BY ISOMERIZING 1,5-CYCLOOCTADIENE

[75] Inventors: Henry R. Menapace, Stow; Neil A. Maly, Tallmadge, both of Ohio

[73] Assignee: The Goodyear Tire & Rubber Company, Akron, Ohio

[22] Filed: Mar. 7, 1973

[21] Appl. No.: 338,771

Related U.S. Application Data

[63] Continuation of Ser. No. 219,527, Jan. 20, 1972, abandoned.

[52] U.S. Cl. .................. 260/666 PY; 260/666 A
[51] Int. Cl.$^2$ .................................. C07E 13/00
[58] Field of Search ............... 260/666 PY, 666 A

[56] References Cited

UNITED STATES PATENTS 3,471,581  10/1969  Maxfield .................... 260/666 PY
3,912,786  10/1975  Wilke et al. ................. 260/666 PY

FOREIGN PATENTS OR APPLICATIONS 2,063,149  7/1972  Germany ..................... 260/666 PY

*Primary Examiner*—Veronica O'Keefe
*Attorney, Agent, or Firm*—F. W. Brunner; H. C. Young, Jr.

[57] ABSTRACT

There is disclosed a method for isomerizing cyclic olefinic hydrocarbons to bicyclic olefins by contacting the cyclic olefins with a catalyst comprised of at least (1) a nickel compound selected from the class consisting of nickel salts of carboxylic acids and organonickel complexes and (2) at least one co-catalyst consisting of organoaluminum compounds or aluminum trihalides at atmospheric pressure and ambient temperatures.

2 Claims, No Drawings

BICYCLO-[3'3'0]-OCTA-2-ENE FORMED BY ISOMERIZING 1,5-CYCLOOCTADIENE

This is a continuation of application Ser. No. 219,527 filed Jan 20, 1972, now abandoned.

This invention relates to the isomerization of hydrocarbons and particularly to the isomerization of cyclic diolefins to bicyclic olefins. It relates to catalysts employed to shift and rearrange double bonds in cyclic diolefins to form bicyclic olefinic compounds.

In many instances it is desirable to shift double bonds within an olefin and many times it is desirable to make a bicyclic compound from a single cyclic diolefinic compound. Processes for shifting double bonds and isomerizing diolefins are known. However, most of these prior art methods of isomerization have some side effects which are undesirable. For instance, some of the prior art processes produce or promote side reactions of the reactants and/or the product of the isomerization to form unwanted end products and thereby result in low efficiencies, problems in separation and for this reason are uneconomical. Still others of these processes use harsh conditions which make them awkward to handle.

Therefore, it is the object of this invention to provide a process for the catalytic isomerization of a cyclic diolefinic hydrocarbon to form bicyclic hydrocarbons. Another object is to provide a process which will isomerize cyclic diolefins in high yields. Still other objects are to provide a process which possesses high selectivity of the desired isomeric form of the diolefin while at the same time minimizing the undesirable side reactions.

According to the invention, cyclic diolefins can be isomerized to bicyclic olefins by means of contacting with a catalyst comprising (1) a soluble nickel compound selected from the class consisting of nickel salts of carboxylic acids and organonickel complexes, and (2) a co-catalyst selected from the class consisting of organoaluminum compounds or aluminum trihalides.

It has been found that when the two catalytic components are brought into contact with the cyclic diolefinic hydrocarbon that a bicyclic hydrocarbon is formed.

The nickel compounds useful in this invention are nickel salts of carboxylic acids. Some of the types of carboxylic acids useful in this invention are acyclic, aromatic, alicyclic, arylalicyclic and dibasic. Representative of these types of acids useful to form these salts are acetic, propanoic, 2-ethyl hexanoic, hexanoic, heptanoic, octanoic, 3-pentenoic, $\alpha,\alpha'$-dimethylhexanoic and decanoic. Also included are acids such as benzoic, toluic-, para-chlorobenzoic and naphthylcarboxylic. Also included are acids such as benzoic, toluic-, para-chlorobenzoic and naphthylcarboxylic. Also included are acids such as cyclopentane carboxylic, 2-methylcyclopentane carboxylic, cyclohexane carboxylic, 2,4-dimethylcyclohexane carboxylic and cycloheptane carboxylic. Also included are such acids as 2-phenylcyclohexane carboxylic, phenylcyclohexylacetic and 2-naphthylcyclohexane carboxylic. Also included are malonic, maleic, fumaric and phthallic acids. The preferred nickel salt is the nickel octanoate.

Some nickel complexes of diketones are also useful. Representative of these types of diketones useful to form the nickel complexes are: 2,4-pentanedionate, dibenzoylmethane, 3-methyl-2,4-pentanedionate, 1-ethoxy, 1,3-butanedionate, 1,3-diethoxy-1,3-propanedionate, 1,3-diphenyl, 1,3-propanedionate and diethyl malonate.

The co-catalysts useful in this invention are organoaluminum compounds selected from the group of halogenated alkyl aluminums or aluminum trihalides. Representative of these types of compounds are diethyl aluminum chloride, di-n-propyl aluminum chloride, ethyl aluminum dichloride, n-propyl aluminum dichloride, diethyl aluminum bromide, n-propyl aluminum dibromide, ethyl aluminum sesquichloride, aluminum trichloride, aluminum tribromide and the like.

A ligand may be employed in the use of this invention. The ligand appears to change the selectivity to the desired product only slightly. "Ligand" is defined as an ion or molecule bound to and considered bonded to a metal atom or ion.

This two component catalyst system has isomerization activity over wide range of catalyst concentration and catalyst ratios. The two catalyst components interreact to form the active catalyst. As a result, the optimum concentration for any one catalyst is very dependent upon the concentration of the other component. Furthermore, while isomerization will occur over a wide range of catalyst concentrations and ratios, the most desirable selectivities and rates are obtained over a narrower range. Isomerization can occur while the mole ratio of the aluminum compound to the nickel compound ranges from about 0.5/1 to about 500/1. The preferred mole ratios of the aluminum compound to the nickel compound ranges from about 2/1 to about 500/1. The preferred mole ratios of the aluminum compound to the nickel compound ranges from about 2/1 to about 100/1.

However, the minimum amount of catalyst at which isomerization will occur is at a ratio of the monomer to the nickel compound of about 4000/1.

The concentration of the catalyst employed depends on factors such as purity, rate desired, temperature and other factors. Therefore, specific concentrations cannot be set forth except to say that catalytic amounts are used.

In general, the isomerizations of this invention can be performed while the cyclic diolefins are dissolved in an inert solvent. By the term "inert" is meant that the solvent does not enter the isomerization reaction or affect it adversely. Representative of such solvents are saturated paraffins and aromatic hydrocarbons such as hexane or benzene. The isomerizations can also be run without any solvent in the presence of the cyclic diolefin.

It is usually desirable to conduct the isomerization employing air-free and moisture-free techniques.

An advantage of this invention is the temperature usually employed in the isomerization is not as high as the temperatures and pressures necessary for prior art isomerization reactions. These isomerizations can be conducted at atmospheric pressure and ambient temperature. Prior art methods require 50 to 200 atmospheres and temperatures from 100° to 250° C. as their operating conditions. In this invention temperatures as low as 0° C. can be readily utilized. It should be made clear that one can go as high in temperature and pressure as desired, but the advantage and novelty of the invention is the use of ambient temperatures and pressure. There is no pressurized atmosphere required in this invention. The isomerizations can safely be run in glass bottles. At room temperatures, the isomerization reactions in this invention can be run almost quantitatively to 100 percent bicyclic olefins within one hour.

EXAMPLE I

The 1,5-cyclooctadiene was distilled from sodium in order to purify it and 12 milliliters (98 millimoles) was charged to 4-ounce bottles containing 10 milliliters of toluene. The catalysts added were (1) nickel octanoate (NiOct) as a solution, 1 milliliter (0.2 millimoles) and (2) ethylaluminum sesquichloride ($Et_3Al_2Cl_3$), as a solution, 3.20 milliliters (4.0 millimoles). The bottles were tightly capped and then agitated at room temperature on a Burrell Wrist-Action shaker for the times shown. The exothermic reactions were terminated by the addition of water. The isomerization products were analyzed by vapor phase chromatography. All percentages are based upon the starting monomer to be isomerized, plus all the product peaks that appear on the VPC chart (vapor phase chromatography).

In this isomerization, 1,5-cyclooctadiene was isomerized to a conversion of 98.4% with a selectivity to bicyclo [3.3.0] oct-2-ene of 94.6%. Reaction time was one hour.

EXAMPLE II

The procedure used is the same as Example I except that the nickel octanoate was left out. In this isomerization, the 1,5-cyclooctadiene was isomerized to a conversion of only 2% with a selectivity to bicyclo [3.3.0] oct-2-ene of 79%. Reaction time was 72 hours.

EXAMPLE III

The same bottle used in Example II was used in this experiment and 0.2 millimoles of nickel octanoate was added to the bottle. After one hour, conversion was 93.7% with a selectivity to bicyclo [3.3.0] oct-2-ene of 98.6%.

EXAMPLE IV

The procedure used is the same as Example I except the co-catalyst is ethyl aluminum dichloride ($EtAlCl_2$) instead of ethylaluminum sesquichloride.

In this isomerization, 1,5-cyclooctadiene was isomerized to a conversion of 94.8% with a selectivity to bicyclo [3.3.0] oct-2-ene of 99.3%. Reaction time one hour.

EXAMPLE V

The procedure used is the same as Example I except the co-catalyst is aluminum trichloride ($AlCl_3$) instead of ethyl aluminum sesquichloride ($Et_3Al_2Cl_3$).

In this isomerization, 1,5-cyclooctadiene was isomerized to a conversion of 99.5% with a selectivity to bicyclo [3.3.0] oct-2-ene of 99.6%. Reaction time was 1 hour.

EXAMPLE VI

The procedure used is the same as Example I, except 0.4 millimoles of triphenylphosphine was added before adding the co-catalyst.

In this isomerization, 1,5-cyclooctadiene was isomerized to a conversion of 34% with a selectivity to bicyclo [3.3.0] oct-2-ene of 95%. Reaction time was 24 hours.

Some other representative examples of cyclic diolefins which can be isomerized in this invention are 1,5-cyclononadiene, 1,4-cycloheptadiene, 1,4-cyclohexadiene, 1,3-cyclohexadiene, 2,5-dimethyl, 1,5-cyclooctadiene and 1-methyl-1,5-cyclooctadiene.

While certain representative embodiments and details have been shown for the purpose of illustrating the invention, it will be apparent to those skilled in this art that various changes and modifications may be made therein without departing from the spirit or scope of the invention.

What we claim is:

1. A process which comprises isomerizing 1,5-cyclooctadiene to bicyclo-[3.3.0]-octa-2-ene by contacting 1,5-cyclooctadiene with a catalyst of (1) a soluble nickle compound selected from at least one of the group consisting of nickel salts of carboxylic acids and (2) a co-catalyst selected from at least one of the group consisting of alkylaluminum dichloride, alkylaluminum sesquichloride and aluminum trichloride.

2. A process which comprises isomerizing 1,5-cyclooctadiene to bicyclo-[3.3.0]-octa-2-ene by contacting 1,5-cyclooctadiene with a catalyst of (1) nickel octanoate and (2) a co-catalyst selected from at least one of the group consisting of ethylaluminum dichloride, ethylaluminum sesquichloride and aluminum trichloride.

* * * * *